(12) United States Patent
Sholev

(10) Patent No.: US 8,435,171 B2
(45) Date of Patent: May 7, 2013

(54) INTERFACE BETWEEN A SURGEON AND AN AUTOMATED ASSISTANT AND METHOD THEREOF

(75) Inventor: Mordehai Sholev, Amikam (IL)

(73) Assignee: M.S.T. Medical Surgery Technologies Ltd., Upper Nazareth (IL)

( * ) Notice: Subject to any disclaimer, the term of this patent is extended or adjusted under 35 U.S.C. 154(b) by 498 days.

(21) Appl. No.: 12/652,131

(22) Filed: Jan. 5, 2010

(65) Prior Publication Data

US 2010/0121149 A1 May 13, 2010

Related U.S. Application Data

(63) Continuation-in-part of application No. PCT/IL2008/000994, filed on Jul. 17, 2008.

(60) Provisional application No. 61/144,760, filed on Jan. 15, 2009.

(30) Foreign Application Priority Data

Jul. 17, 2007 (IL) .......................................... 184664

(51) Int. Cl.
*A61B 1/00* (2006.01)
*A61B 5/05* (2006.01)

(52) U.S. Cl.
USPC ........................................... 600/117; 600/424

(58) Field of Classification Search .................. 600/117, 600/424
See application file for complete search history.

(56) References Cited

U.S. PATENT DOCUMENTS

| 5,211,165 A * | 5/1993 | Dumoulin et al. ............ 600/410 |
| 6,714,841 B1 | 3/2004 | Wright et al. |
| 2004/0015053 A1* | 1/2004 | Bieger et al. .................. 600/117 |
| 2005/0090711 A1 | 4/2005 | Fuchs |
| 2008/0108872 A1* | 5/2008 | Glukhovsky et al. ......... 600/117 |

OTHER PUBLICATIONS

A Model for Estimating the Real-Time Position of a moving Object . . . (Arshak et al.).

* cited by examiner

*Primary Examiner* — W. B. Perkey
(74) *Attorney, Agent, or Firm* — The Law Office of Michael E. Kondoudis

(57) ABSTRACT

An interface between a surgeon and an automated assistant, including: at least one array comprising N RF transmitters, where N is a positive integer; at least one RF receiver provided with at least two directional antenna; means for attaching said RF transmitter array to at least one surgical tool; and a computerized operating system adapted to record the received signal strength (RSS) received by each antenna of the one RF receiver and to calculate therefrom the position of each of the N RF transmitters, and further adapted to provide automatically the results of the calculation to the surgeon.

20 Claims, 13 Drawing Sheets

INTERFACE BETWEEN A SURGEON AND AN AUTOMATED ASSISTANT AND METHOD THEREOF

CROSS REFERENCE TO RELATED APPLICATIONS

This application is a continuation-in-part application of International Application No. PCT/IL/2008/000994, filed Jul. 17, 2008, which, in turn, claimed the benefit of Israeli Patent Application No. 184664, filed Jul. 17, 2007, the contents of which are incorporated by reference. In addition, this application further claims the benefit of U.S. Provisional Patent Application No. 61/114,760, filed Jan. 15, 2009, the content of which is incorporated by reference herein.

TECHNICAL FIELD

This patent relates generally to endoscope guided surgical instruments and procedures, and in particular to interfaces that allow identification of the spatial position of a laparoscope during endoscopic surgery.

BACKGROUND ART

During laparoscopic surgery it is often required to shift the spatial placement of the endoscope in order to present the surgeon with an optimal view. Conventional laparoscopic surgery makes use of either human assistants who manually shift the instrumentation or alternatively of robotic automated assistants. Automated assistants utilize interfaces that enable the surgeon to direct the mechanical movement of the assistant, achieving a shift in the camera view. U.S. Pat. No. 6,714,841 discloses an automated camera endoscope in which the surgeon is fitted with a head mounted light source that transmits his head movements to a sensor, forming an interface that converts said movements to directions for the mechanical movement of the automated assistant. Alternative automated assistants incorporate a voice operated interface, a directional key interface, or other navigational interfaces. The main disadvantage of the above interfaces is that they are based on cumbersome operations for starting and stopping movement directions that requires the surgeon's constant attention.

An article titled "*A method for estimating the real time Positions of a moving object in wireless telemetry applications using RF sensors*" by K. Arshak was recently published. The article relates to locating a transmitting object using multiple receiving antenna sensors located at various place surrounding the transmitting device. The receiver antennas are assumed to be omni directional and the location of the transmitter is achieved through distance estimation (i.e., triangulation) from each of the receiving antenna.

The distance from the transmitter is estimated by measuring the received signal strength (RSS) of the received signal:

$$RSS = P_T - P_L(d_0) - 10\eta \log_{10}(d/d0) + X_\sigma,$$

calculated in decibel, $P_T$ is the transmitted power, $P_L(d_0)$ is the path loss for a reference distance $d_0$, $\eta$ is the pass loss exponent, d is the distance between the transmitter and the receiver and $X_\sigma$ is a Gaussian random variable.

Therefore, the signal received is proportional to transmit power ($P_T$), the $\eta$ power of distance to the transmitter, normally in free space $\eta=2$, if all is known except the distance, it can be resolved from the above mentioned equation, a distance can be calculated from each of the receiving antenna. The object (transmitter) location is at the intersection of spheres with every distance which is the respective sphere radius (i.e., Triangulation).

Arshak states in the article that other method such as time of arrival, time differences of arrival and angle of arrival are not feasible due to dense multipath environment. Yet more, if the transmit power is unknown, unstable or inaccurate; or if the propagation factor is unknown then Arshak's method won't be valid.

Therefore there is still a long felt need for a method which will enable the relative position of the transmitter (and thus the medical instrument).

Research has suggested that these systems divert the surgeons focus from the major task at hand. Therefore technologies based on various kinds of positioning systems have been developed to simplify interfacing control. These technologies still fail to address another complicating interface aspect of laparoscopic surgery, however, as they do not allow the surgeon to signal both to the automated assistant and to surgical colleagues on which surgical instrument his attention is focused.

Thus, there is a long-felt need for a device that would allow the surgeon to identify to the laparoscopic computing system as well as to surgical colleagues to which surgical instrument attention is to be directed, thereby directing the view provided by the endoscope to the selected area of interest.

SUMMARY OF THE INVENTION

Therefore, in accordance with a preferred embodiment of the present invention, it is an object of the present invention to disclose an interface between a surgeon and an automated assistant, comprising (a) at least one array comprising N RF transmitters, where N is a positive integer; (b) one RF receiver, provided with at least two directional antenna; (c) means for attaching said RF transmitter array to at least one surgical tool; and, (d) a computerized operating system adapted to record the received signal strength (RSS) received by said RF receiver and to calculate therefrom the position of each of said N RF transmitters, and further adapted to provide automatically the results of said calculation to the human operator of said interface. It is within the essence of the invention wherein said computerized operating system calculates at least one of the parameters chosen from the group consisting of (a) the angle from which the signal had been received; (b) the spatial location of said at least one surgical tool; (c) the path of said at least one surgical tool; (d) the spatial location of the point of insertion of said at least one surgical tool into the body of a patient; (e) the spatial location of the tip of said at least one surgical tool; (f) matching each RF transmitter code with each calculated spatial location of said at least one surgical tool and/or said tip of said at least one surgical tool, and further wherein said computerized operating system provides automatically the results of said calculation to the human operator of said interface.

It is a further object of this invention to disclose such an interface, further comprising an endoscopic device.

It is a further object of this invention to disclose such an interface, wherein said endoscopic device comprises optical imaging means, and further wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) the predicted appearance of said at least one surgical tool within said optical image; (g) if more than one of said at least one surgical tools appears simultaneously in said optical image, distinguishing among said more than at least surgical tools appearing in said optical image, and further wherein said computerized operating system provides automatically the results of said calculation to the human operator of said interface.

It is a further object of this invention to disclose such an interface, further comprising (a) a automated assistant for said endoscopic device; and (b) means for interfacing said computerized operating system to said automated assistant. It is within the essence of the invention wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) a desired new location for said endoscopic device; (g) command protocol means for directing said automated assistant via said interface to maneuver said endoscopic device to a desired new location, and further wherein said computerized operating system provides automatically the results of said calculation to the human operator of said interface.

It is a further object of this invention to disclose such an interface, wherein said endoscopic device comprises optical imaging means, and further wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) the predicted appearance of said at least one surgical tool within said optical image; (g) if more than one of said at least one surgical tools appears simultaneously in said optical image, distinguishing among said more than at least surgical tools appearing in said optical image; (h) a desired new location for said optical imaging means; (i) a command protocol for directing said automated assistant via said interface to maneuver said endoscopic device to a desired new location, and further wherein said computerized operating system provides automatically the results of said calculation to the human operator of said interface.

It is a further object of this invention to disclose such an interface, wherein said computer controller additionally transmits a command protocol to said automated assistant via said interface to maneuver said endoscopic device to a desired new location.

It is a further object of this invention to disclose such an interface, wherein said interface is adapted for manual operation, whereby each of said N transmitters transmits in response to a command signal from the human operator of the interface.

It is a further object of this invention to disclose such an interface, wherein said interface is adapted for automatic operation, whereby each of said N transmitters transmits continuously.

It is a further object of this invention to disclose such an interface, wherein said interface is adapted for automatic operation, whereby each of said N transmitters transmits continuously and further wherein said computer transmits said calculated parameters for each of said N transmitters in response to a command signal from the human operator of the interface.

It is a further object of this invention to disclose such an interface, wherein said antenna array comprises at least one directional antenna.

It is a further object of this invention to disclose such an interface, wherein said transmitters transmit in the 430 MHz ISM band.

It is a further object of this invention to disclose such an interface, wherein M=1, and further wherein said receiver array is adapted to determine the angle whose vertex is the location of said antenna array and which is subtended by the line connecting any two of said N transmitters.

It is a further object of this invention to disclose such an interface, wherein said interface comprises M receivers, M is an integer higher than 1; and further wherein said M receivers are adapted to determine the location of each of said N transmitters by triangulation.

It is a further object of this invention to disclose such an interface, wherein said transmitters transmit a modulated signal, said modulation chosen from the group consisting of (a) frequency modulation, (b) amplitude modulation.

It is a further object of this invention to disclose such an interface, wherein said modulation occurs at a frequency of about 1.5 kHz.

It is a further object of this invention to disclose such an interface, wherein each of said N RF transmitters is modulated at a different frequency.

It is a further object of this invention to disclose such an interface, wherein said N modulation frequencies are chosen from the band of frequencies spanning the range of from about 1.0 kHz to about 1.5 kHz.

It is a further object of this invention to disclose such an interface, wherein receiver is a single conversion receiver.

It is a further object of this invention to disclose a method for calculating positional parameters of a laparoscopic surgical tool, comprising the steps of (a) obtaining an interface for a laparoscope, said interface comprising (i) at least one array comprising N RF transmitters, where N is a positive integer, (ii) one RF receiver provided with at least two directional antenna; (iii) a computerized operating system adapted to record the received signal strength RSS received by each antenna of said RF receiver and to calculate therefrom the position of each of said N RF transmitters, and further adapted to provide automatically the results of said calculation to the human operator of said interface; (b) obtaining a surgical tool; (c) attaching said RF transmitter array to said surgical tool; (d) measuring the received signal strength (RSS) from said N RF transmitters received at each of said directional antenna of said RF receivers; and (e) calculating spatial parameters relating to each of said N transmitters according to a predetermined protocol. It is in the essence of the invention wherein said step of calculating said parameters of each of said N transmitters yields positional parameters of said laparoscope surgical tool, said positional parameters is selected from a group consisting of (a) the angle from which the signal had been received; (b) the spatial location of said at least one surgical tool; (c) the path of said at least one surgical tool; (d) the spatial location of the point of insertion of said at least one surgical tool into the body of a patient; (e) the spatial location of the tip of said at least one surgical tool; (f) matching each RF transmitter code with each calculated spatial location of said at least one surgical tool and/or said tip of said at least one surgical tool, and further wherein said computerized operating system provides automatically the results of said calculation to the human operator of said interface.

It is a further object of this invention to disclose a method for controlling the position of an endoscopic device, comprising the steps of (a) obtaining an interface between a surgeon and an automated assistant, said interface comprising (i) at least one array comprising N RF transmitters, where N is a positive integer, (ii) one RF receiver provided with at least two directional antenna; (iii) a computerized operating system adapted to record the received signal strength RSS received by each antenna of said RF receiver and to calculate therefrom the position of each of said N RF transmitters, and further adapted to provide automatically the results of said calculation to the human operator of said interface; (iv) an automated assistant for said endoscopic device; and, (v) means for interfacing said computerized operating system to said automated assistant; (b) obtaining a surgical tool; (c) attaching said RF transmitter array to said surgical tool; (d) measuring the received signal strength (RSS) from said N RF transmitters received at each of said directional antenna of said RF receivers; (e) calculating spatial parameters relating to location of each of said N transmitters; (f) calculating a desired new position for said endoscopic device; (g) sending a command from said computerized operating system to said automated assistant via said interfacing means to maneuver said endoscopic device to said desired new location; and, (h) maneuvering said endoscopic device to said desired new location It is in the essence of the invention wherein said step of calculating said parameters of each of said N transmitters yields positional parameters of said laparoscope surgical tool, said positional parameters is selected from a group consisting of (a) the angle from which the signal had been received; (b) the spatial location of said at least one surgical tool; (c) the path of said at least one surgical tool; (d) the spatial location of the point of insertion of said at least one surgical tool into the body of a patient; (e) the spatial location of the tip of said at least one surgical tool; (f) matching each RF transmitter code with each calculated spatial location of said at least one surgical tool and/or said tip of said at least one surgical tool, and further wherein said computerized operating system provides automatically the results of said calculation to the human operator of said interface.

It is a further object of this invention to disclose such an interface, wherein said endoscopic device comprises optical imaging means, and further comprising the additional steps of (a) determining said position of said surgical tool relative to the image frame; and (b) maneuvering said optical imaging means such that said surgical tool appears at a predetermined location within said image frame.

It is a further object of this invention to provide such a method, wherein each of said N transmitters transmits in response to a signal from the human operator of said interface.

It is a further object of this invention to provide such a method, wherein each of said N transmitters transmits continuously.

The device of the present invention has many technological advantages, among them:

Simplifying the communication interface between surgeon and automated assistants.
Seamless interaction with conventional computerized automated endoscope systems.
Simplicity of construction and reliability.
User-friendliness.
Additional features and advantages of the invention will become apparent from the following drawings and description.

BRIEF DESCRIPTION OF DRAWINGS

For a better understanding of the invention with regard to the embodiments thereof, reference is made to the accompanying drawings (not to scale), in which like numerals designate corresponding sections or elements throughout, and in which.

DETAIL DESCRIPTION OF THE INVENTION

Figure 1A:
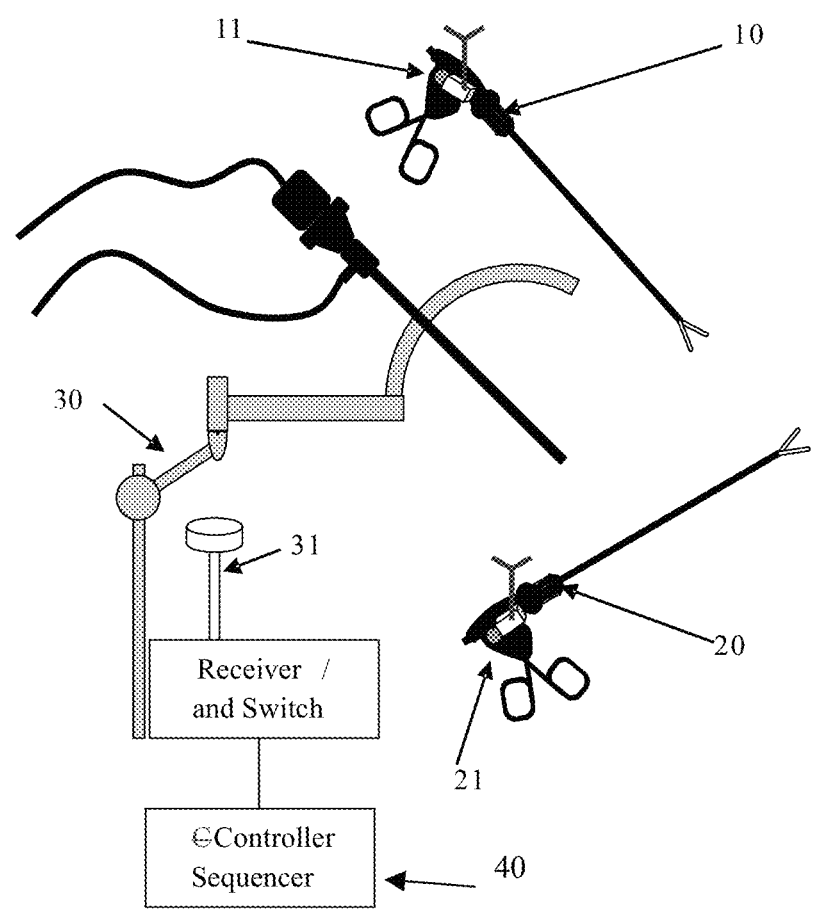
FIG. 1A shows a general schematic view of surgical tool positioning system that detects the location of a surgical tool at the time the surgeon activates the surgical tool transmitter (manual mode)

The present invention is utilized to improve upon the interface between surgeon and automated assistants by communicating the surgeon's current instrument of choice, supplying location data to the image processing computing software thereby directing the endoscope to focus on said choice. The technology relies on marrying a conventional laparoscopic system with data obtained from small RF transmitters attached to a surgical tool. It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of said claims.

The present invention provides an interface between a surgeon and an automated assistant, comprising (a) at least one array comprising N RF transmitters, where N is a positive integer; (b) one RF receiver, said receiver provided with at least one directional antenna; (c) means for attaching said RF transmitter array to at least one surgical tool; and, (d) a computerized operating system adapted to record the relative signal strength received by said RF receiver and to calculate therefrom the position of each of said N RF transmitters, and further adapted to provide automatically the results of said calculation to the human operator of said interface. It is within the essence of the invention wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool, and further wherein said computerized operating system provides automatically the results of said calculation to the human operator of said interface.

As used herein, the term 'automated assistant' refers to any mechanical device (including but not limited to a robotic device) that can maneuver and control the position of a surgical or endoscopic instrument, and that can in addition be adapted to receive commands from a remote source.

As used herein, the term 'Antenna Gain' refers to the ratio of the radiation intensity of an antenna in a given direction to the intensity that would be produced by a hypothetical ideal antenna that radiates equally in all directions (isotropically) and has no losses.

As used herein, when referring to transmission of information to a human, the term 'provide' refers to any process (visual, tactile, or auditory) by which an instrument, computer, controller, or any other mechanical or electronic device can report the results of a calculation or other operation to a human operator.

As used herein, the term 'automatic' or 'automatically' refers to any process that proceeds without the necessity of direct intervention or action on the part of a human being.

In one of the preferred embodiments of the invention, any desired surgical instrument is fitted with an RF transmitter, and selection is achieved by depressing its button.

The invention describes two methods of operation:

A manual method, in which a transmitter emits RF signal only when the surgeon presses a button located e.g., on one of the arms (either left or right—but not both simultaneously), the system then indicating the direction of that arm; and, An automatic method, in which all transmitters continuously emit RF signal and the system tracks the direction of all transmitters simultaneously. When the surgeon presses a button of one of the transmitters, the system output is the direction and location of the specific transmitter.

The term "about" refers hereinafter to a range of 25% below or above the referred value. The automatic mode has some advantages over the manual mode because the system can make use of history track files in order to filter the data and apply prediction algorithms. The continuous stream of data also allows the software to compute additional important data such as the insertion point of each tool, and the predicted tools location on the image.

System operation will be explained for both MANUAL- (sequential), and AUTOMATIC (periodic or simultaneous) modes. In order to simplify the explanation a system used to locate the positions and directions of only 2 surgical tools is described, but the method described can be used with minor changes to locate the position of any number of surgical tools used in any laparoscopic surgeries.

Reference is now made to FIG. 1a which schematically describes the surgical tool positioning MANUAL system according to one embodiment of the invention. An antenna 31 is set and a receiver is preferably mounted on, or near, the robotic camera holder. Two identical transmitters, i.e., (i) transmitter 11 mounted on surgical tool 10; and (ii), transmitter 21 mounted on surgical tool 20 are provided. A control and processing function controller 40 is further provided, being either a laptop PC or an embedded controller.

As described above, in the MANUAL system the transmitter emits RF signal only when the surgeon presses upon the surgical instrument the surgeon desires to track. Once the transmitter transmits a signal, the receiver communicates with the controller and instructs the tracking of the medical instrument desired by the surgeon.

Figure 1B:
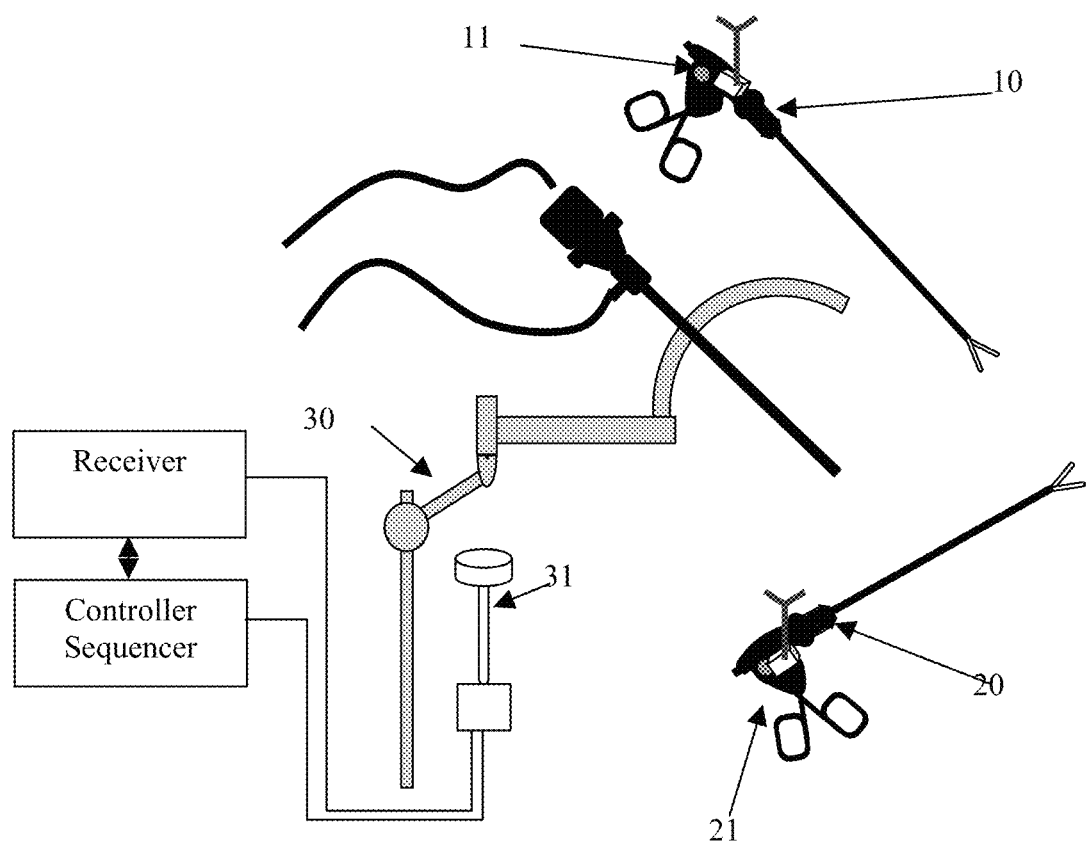
FIG. 1B shows a general schematic view of surgical tool positioning system that detects the location of surgical tools continuously (continuous automatic mode)

Reference is now made to FIG. 1b which schematically describes the surgical tools positioning AUTOMATIC system according to yet another embodiment of the invention.

As described above, in the AUTOMATIC system the transmitter continuously emits RF signals. Therefore, the receiver constantly communicates with the controller.

Figure 2A:
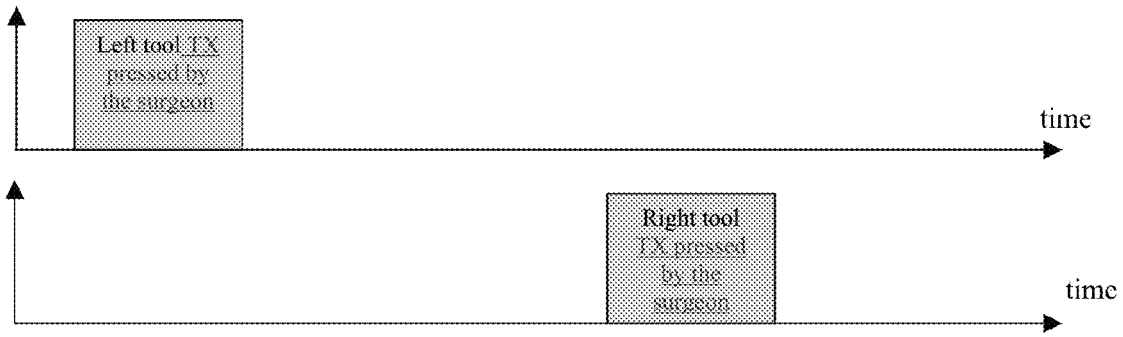
FIG. 2A is a diagram demonstrating sequential transmit operation.
Figure 2B:
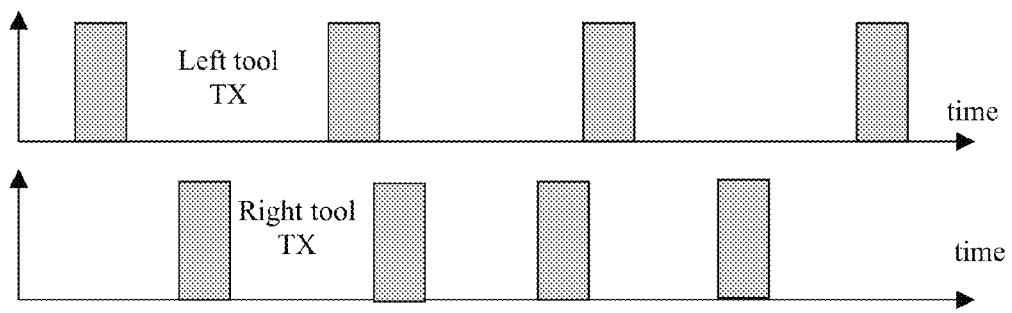
FIG. 2B is a diagram demonstrating periodic transmit operation, with unequal rates for left and right transmitters.
Figure 2C:
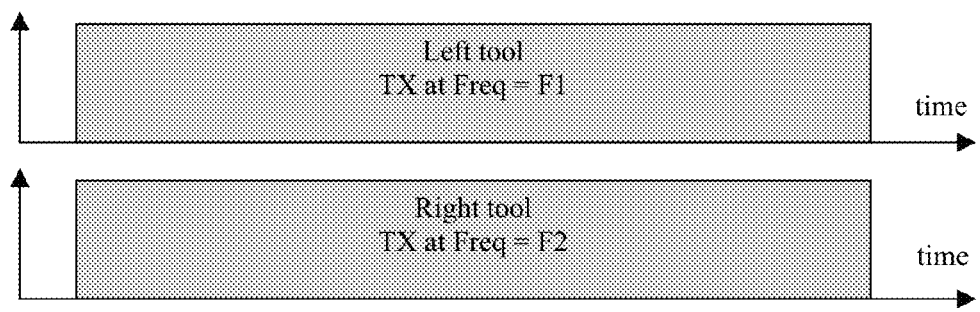
FIG. 2C is a diagram demonstrating simultaneous transmit operation with different frequencies.

The transmitters 11 and 21 can operate in one of three modes: (a) sequential/manual mode, as shown in FIG. 2a, upon the surgeon's pressing an appropriate button (manual mode); (b) periodic/automatic mode as shown in FIG. 2b, in which the transmitters attached to the two tools provide pulsed signals at different pulse rates; or (c) simultaneous/ automatic mode, as shown in FIG. 2c, in which the two transmitters transmit simultaneously and continuously, but at different radio frequencies. In all three modes, the receiver can detect and process individual reception from any one of the two tools and identify which transmission belongs to which tool.

Reference is now made to FIGS. 3, 4a through 4d, and 5, in which further details of the system operation are illustrated.

Figure 7A:
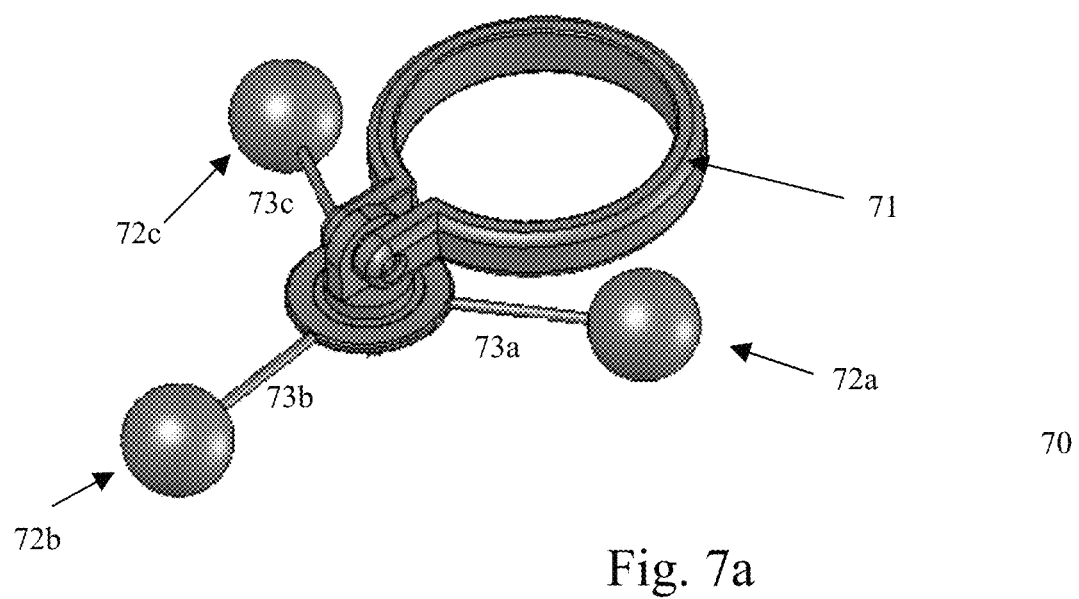
FIG. 7A shows an example of a planar antenna structure.

The receiver receives sequentially the signal of each tool through the antenna set, the antenna set comprising at least one (preferably) multiple directional antennas array as shown in FIG. 7a, where at least one of the antenna is connected to the receiver.

Figure 3A:
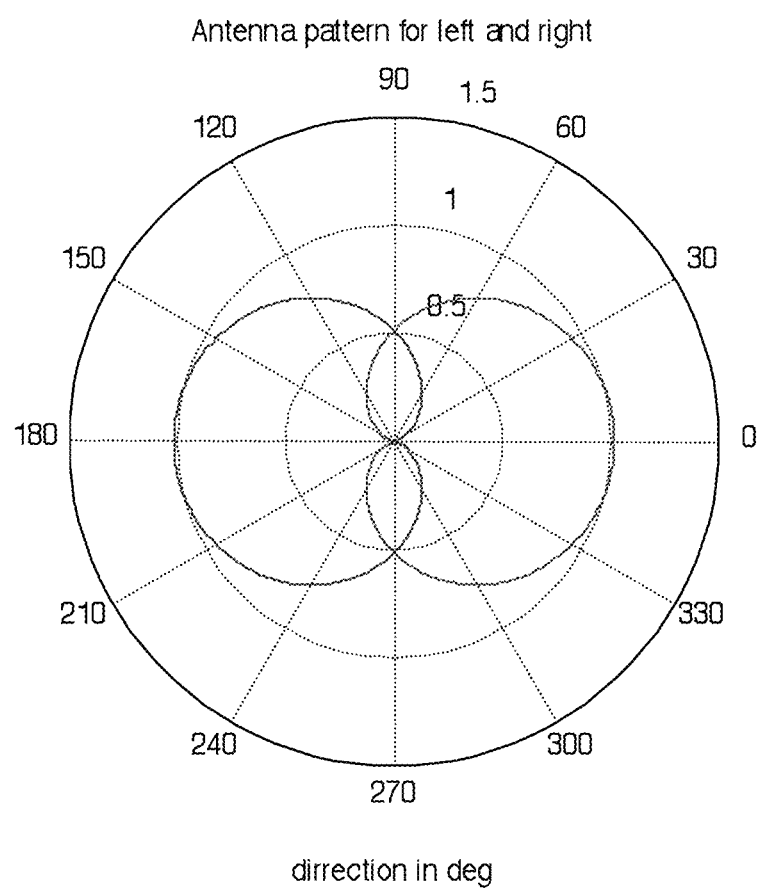
FIGS. 3a and 3b is a schematic view of the antenna pattern.

In order to locate the transmitter, at least two directional patterns are required as illustrated in FIG. 3a. The figure illustrates a typical antenna's pattern as a function of the signal's angle and of the intensity.

Alternatively, the transmitted signal may be modulated (in different embodiments of the invention, either (a) frequency modulation or (b) amplitude modulation or (c) both FM and AM simultaneously). Thus, in order to identify the arm from which the transmission is being received, each transmitter has a different modulation frequency. Hence an easier detection of the arm is enabled.

In general once the correct transmitter has been identified, the following mathematical analysis is performed:

The direction of each transmitter (and hence the desired instrument) is calculated by using a at least one receiver, preferably one receiver, having at least 2 directional antennas, preferably 3.

The received signal strength (RSS) is a function of the distance (d) between the receiver and the transmitter (i.e., the instrument); the strength of the transmitted signal (P); the path loss exponent ($\eta$); and the antenna's gain (Gr).

Since all the antenna are co-located, the ratio of the RSS will be the ratio between the antennas' gain.

Therefore, by knowing how the gain's ratio varies with the angle—one can calculate the angle from which the signal has been transmitted.

The above mentioned mathematical analysis is performed based on the following facts:
1. The method uses several directional antenna that are co-located as a set of receiving antenna; and,
2. The transmitter is assumed to be located somewhere around the receiving antenna set.

As described, the method is adapted to find only the direction of the transmit antenna by comparing the received power from all antenna in the set.

As commonly known, the received power depend on the transmit power ($P_T$), the distance from receiving to transmit antenna (d) and on the receiving antenna gain (Gr(i)) in the direction of the transmitter.

Since the set of antenna are co-located (the transmit power ($P_T$), the distance from receiving to transmit antenna (d) et cetera are eliminated) and the ratio of the receiving signal strength (RSS) is as follows:

$$RSS(antenna_i) - RSS(antenna_k) = Gr(antenna_i) - Gr(antenna_k)$$

As can be seen, the difference in the RSS does not depend upon the transmit power $P_T$ (since the $P_T$ received by each antenna is the same), and it does not depend upon the distance (since the received antenna are co-located).

From the difference set of RSS, the difference in the gain between the receiving antennas is known.

Since the received antenna are directional, the gain pattern is unambiguously depend upon the angular positioning of the transmitter (and hence the instrument). Therefore, the angular position and hence the direction can be resolved in unambiguously manner from the gain difference.

Figure 3B:
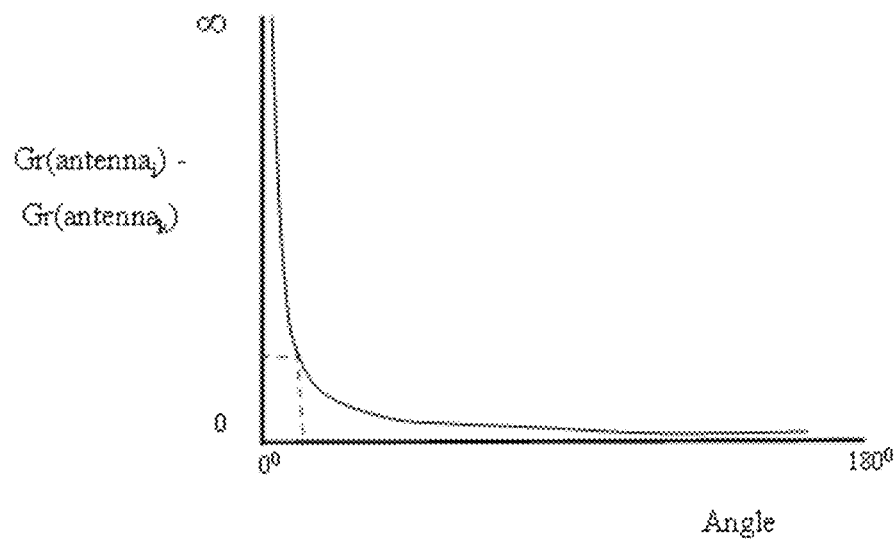

Therefore, by knowing how the gain's ratio varies with the angle—one can calculate the angle from which the signal has been transmitted (see FIG. 3b). As illustrated in FIG. 3b, once the RSS differences is know, the angle is from which the signal is being sent (i.e., the angular location of the transmitter and hence the instrument) can be calculated.

It should be noted that the above mentioned calculation is much less sensitive to multipath environment found whilst applying the methods in laparoscopic surgeries.

Figure 7B:
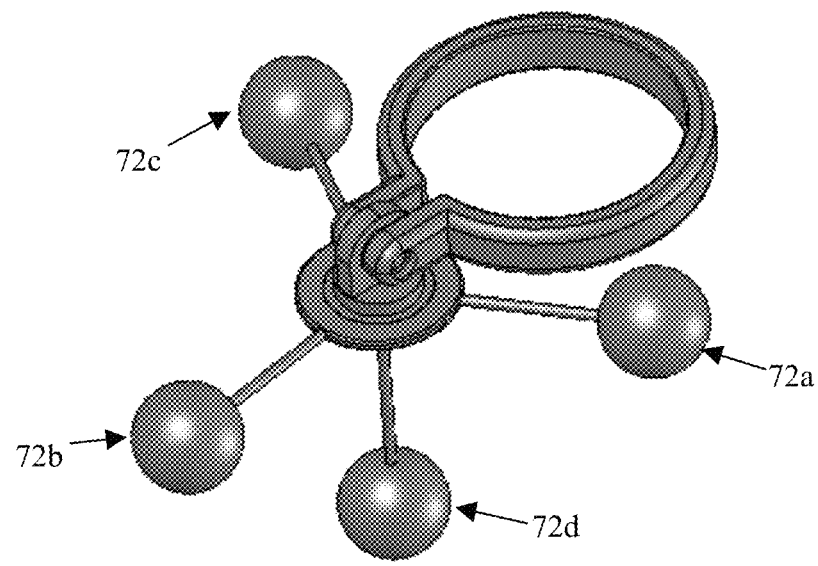
FIG. 7B shows an example of a spatial antenna structure.

According to another embodiment of the invention, the antenna array has more than two patterns, allowing the system to identify the direction of the tool with a finer resolution. Reference is now made to FIG. 7b, in which a non-limiting example of an additional embodiment is illustrated, in which the antenna array comprises four directional patterns: left, right, forward and aft. From the direction from which the strongest reception is received, the system is able to identify the sector in space in which the tool is located. Moreover, from interpolation of the received power from all antenna patterns, even finer directional resolution is possible.

The receiver detects the received signal power for each antenna in the array and reports it to the controller. The controller then resolves the directions of the two tools relative to antenna 31.

Figure 4A:
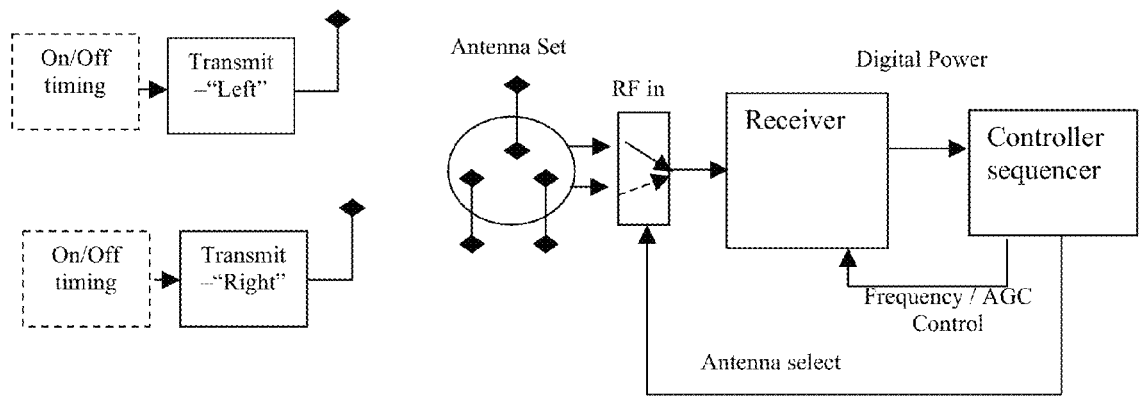
FIG. 4A shows the system block diagram.

Transmitters 11 and 21 shown in FIG. 4a may transmit in a wide range of frequencies; a typical frequency is the ISM band of 430 MHz. Transmission is done at very low power, generally below about 1 mW.

The transmitted signal is modulated (in different embodiments of the invention, either (a) frequency modulation or (b) amplitude modulation or (c) both FM and AM simultaneously). In a preferred embodiment, the modulation is performed at an audio rate of about 1.5 kHz. The transmitter uses a built-in antenna. In order to identify the arm from which the transmission is being received, each transmitter has a different modulation frequency. In a preferred embodiment of the invention, the frequencies are located within the band encompassing the range of from about 1.0 kHz to about 1.5 kHz.

Figure 4B:
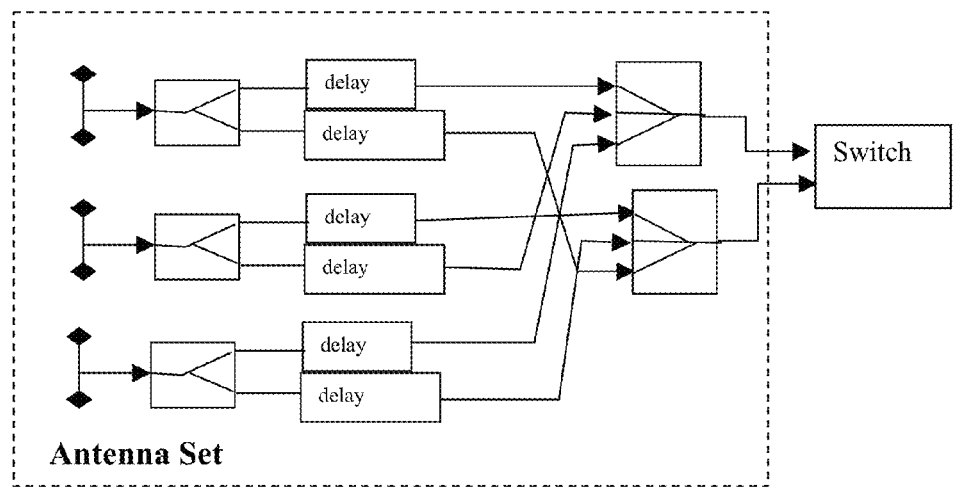
FIG. 4B shows antenna set block diagram.

The signal for each transmitter is received by all antennas in the array (see FIG. 4b above). The antennas in the array typically comprise three very short dipoles mounted on the edge of an equal edge three-legged star or circle, as shown in FIGS. 7a and 7b. The diameter of the circle or three-legged star is about 8 to 12 cm for operation at about 430 MHz. The use of the antenna array to identify the beam pattern is illustrated schematically in FIG. 4b. The antenna pattern is formed by combining the signal received by each antenna with different delays and signal weights. In order to set the pattern, in a typical embodiment, each antenna output is split into several equal power signals and a sample of each antenna signal is combined into one directional output. Which output is being measured is selected by an external switch.

The receiver receives the signal in sequence from each directional pattern and detects the signal power in any pattern for the signals from both tools; from the power ratio the signal direction is calculated. For example, for a two pattern antenna (left and right) if the signal from left antenna is much stronger than from right one, then the signal must have arrived from the left and vice versa. In parallel, the signal modulation as transmitted is detected and the modulation frequency is measured. Since each transmitter has a different modulation frequency, identification of the transmitter from which a particular signal originates is straightforward.

Figure 4C:
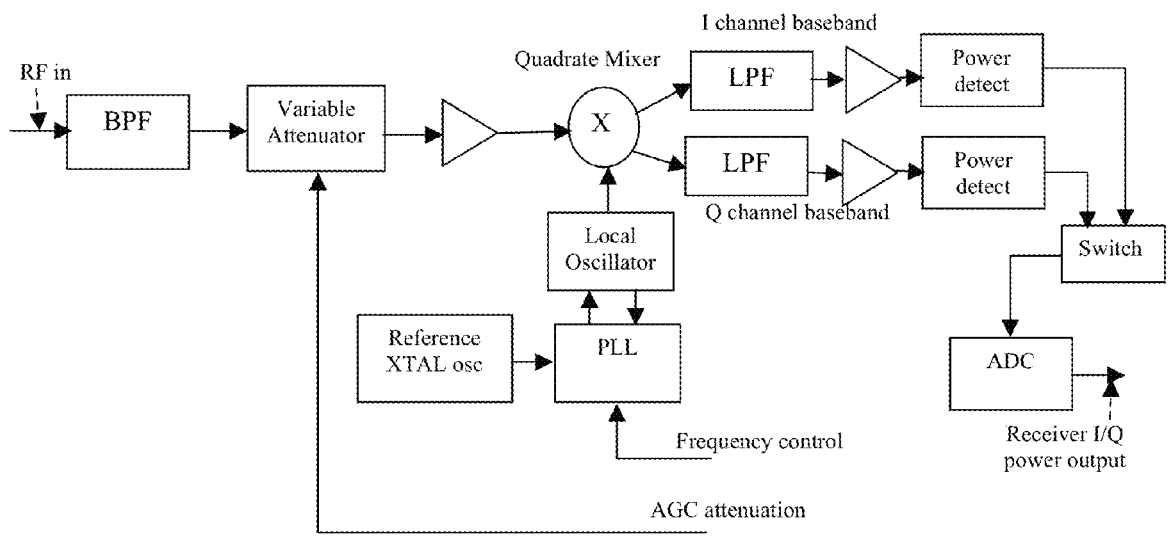
FIG. 4C shows the receiver internal block diagram.

The receiver may be of any type, but in order to reduce the cost, size and power consumption, in a preferred embodiment, the receiver is a single conversion receiver that converts the input signal to base band. The receiver block diagram is shown in FIG. 4c. The receiver operation is as follows: the RF input is filtered around the transmitter frequency band then passed through a variable attenuator controlled by the system controller. Next, it is then amplified and then down converted using a Quadrate mixer and a local oscillator. The mixer outputs are the IF baseband: I (in phase) and Q (Quadrate) outputs, which are filtered by two low pass filters (e.g., about 30 kHz) then amplified. The base band signal powers are then detected. The DC power relative to the signal power is selected in sequence. The analog signal is then passed to an analog to digital converter (ADC), following which the total received power is computed digitally.

In an additional embodiment of the invention (not illustrated), the base band signal is analog to digital converted, so that the power of both the I and the Q channel is converted to a digital value.

The local oscillator frequency is locked by the PLL to the XTAL reference oscillator, controlled by the system controller.

In order to ensure that received signal is within a limited range the receiver gain is adjusted automatically (AGC).

Figure 4D:
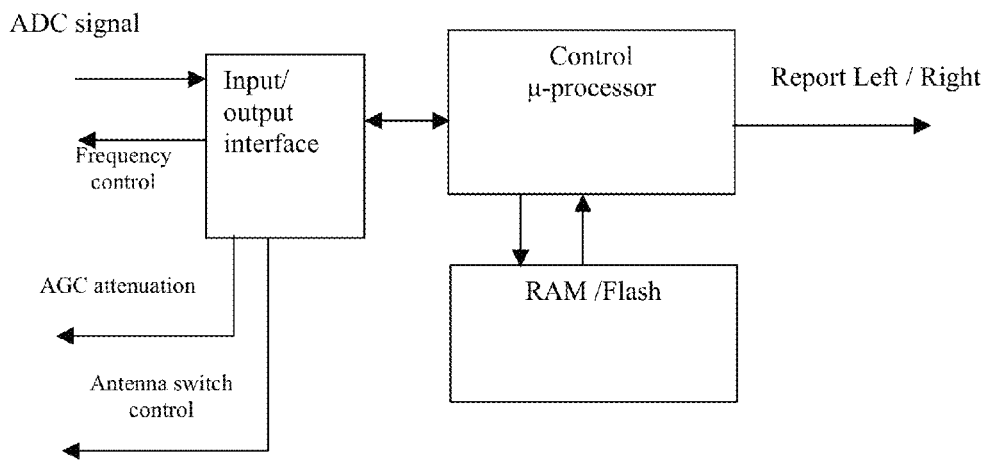
FIG. 4D shows the controller/sequencer block diagram.

Finally, as shown in FIG. 4d, the digital signal power is transferred to the system controller, where the controller calculates from the time of reception from which tool it is received and from which antenna pattern, using the power the controller compute the tool direction for each of the two tools.

The controller includes a timer based sequencer, preferably built into the microprocessor timing unit, that switches the receiver antenna, and in case of multiple frequency transmission, sets the receiver frequency sequentially.

Figure 5:
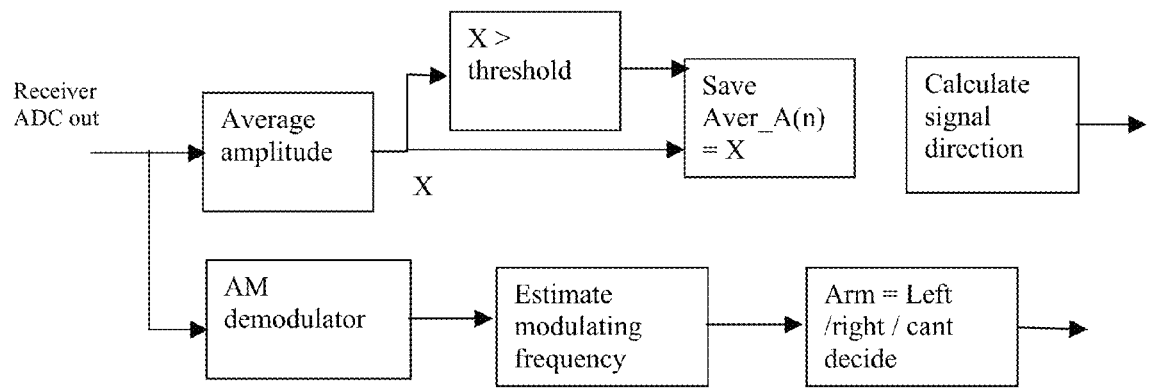
FIG. 5 shows system control software operation flow.

The operation sequence of the system is illustrated schematically in FIG. 5, which shows the system control software operation flow:

[1] The AD signal is averaged to detect the average amplitude, averaging being done over one dwell duration ("X" indicates the output after averaging);

[2] Signal presence is detected when X is above a predetermined threshold;
[3] Average amplitude X is saved in a vector array (Aver_A (n), n={1,2, ... N}) if signal is present, the storage being done on the appropriate antenna number place in the array;
[4] If for a given antenna, signal is present on N successive dwell durations, the signal direction is calculated;
[5] The modulation (in the particular embodiment illustrated, AM) is detected from the signal power input;
[6] The modulation frequency is measured; and,
[7] From the measured frequency, the arm type is detected; in the case of weak signal or simultaneous transmission, the module reports "can't decide," indicating a garbage signal.

In embodiments in which the transmitter operates periodically, both transmitters operate for a fraction of the time then switch off, then switch on again and so on with a constant or random cycle periodicity, each transmitter transmitting with a different transmission pulse cycle time in order to ensure that transmissions will not overlap at all times but only at times separated by $t_1 \cdot t_2$, where $t_1$ and $t_2$ are the pulse cycle times of the two transmitters. In parallel, the receiver sequentially switches the receiver channel among the different antennas and dwells on each antenna for a fixed dwell time. From the level of signal received, the system determines whether or not a signal is present. If a single signal is present either from the right arm or left arm transmitter, the direction of the signal is calculated from the signal strength received from different antennas, and the arm is identified from the internal modulation frequency. In case of coincident simultaneous transmit the receiver cannot identify the signal modulation therefore the measurement is rejected. In an additional embodiment, the system tracks the transmission period cycle of each arm and predicts the simultaneous transmission times in order better to identify which arm's signal is being detected.

Figure 6A:
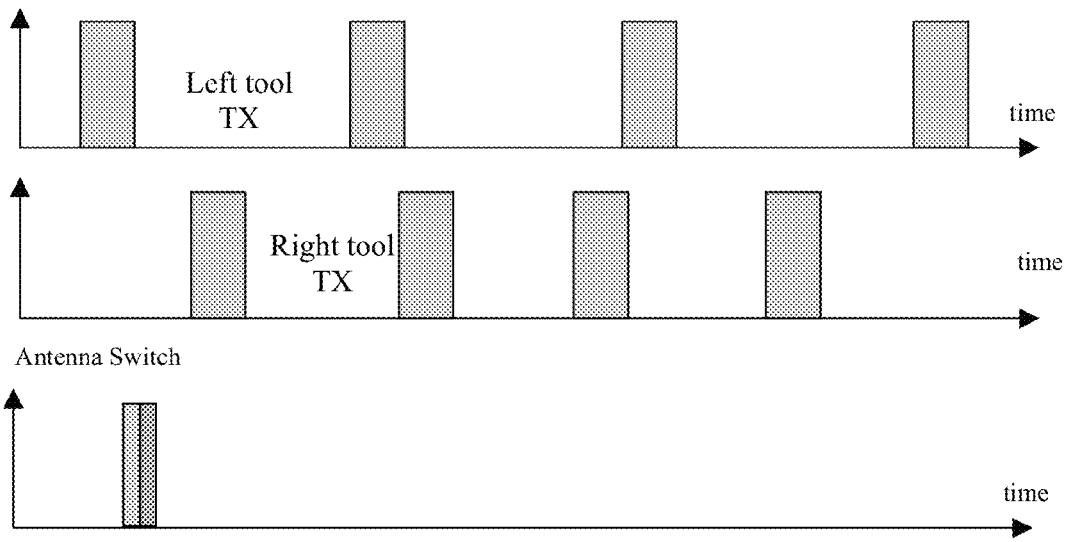
FIG. 6A shows the antenna switching pattern during periodic transmit operation.

In order to ensure that the direction of a single transmission can be calculated (if only a single transmission is received), the "transmit on" duration is at least (N+1) X dwell intervals, where N is the number of antenna outputs. This ensures that the transmission is received during at least N successive dwell times, allowing the system to calculate its direction. For example if the receiver antenna is switched in sequence staying on for 10 ms (i.e., a 10 ms antenna dwell time) in each pattern out of two patterns, then the total antenna switch time cycle is 20 ms, and the transmitter switch on time is required to last for at least 30 msec. For example, in one embodiment of the invention, the transmit on/off cycle times are 120 ms and 150 ms for the left and right arm transmitter respectively. Each transmitter is on for 30 ms and off for the rest of the time. The antenna switch versus transmit periodic operation is shown in FIG. 6a.

Figure 6B:
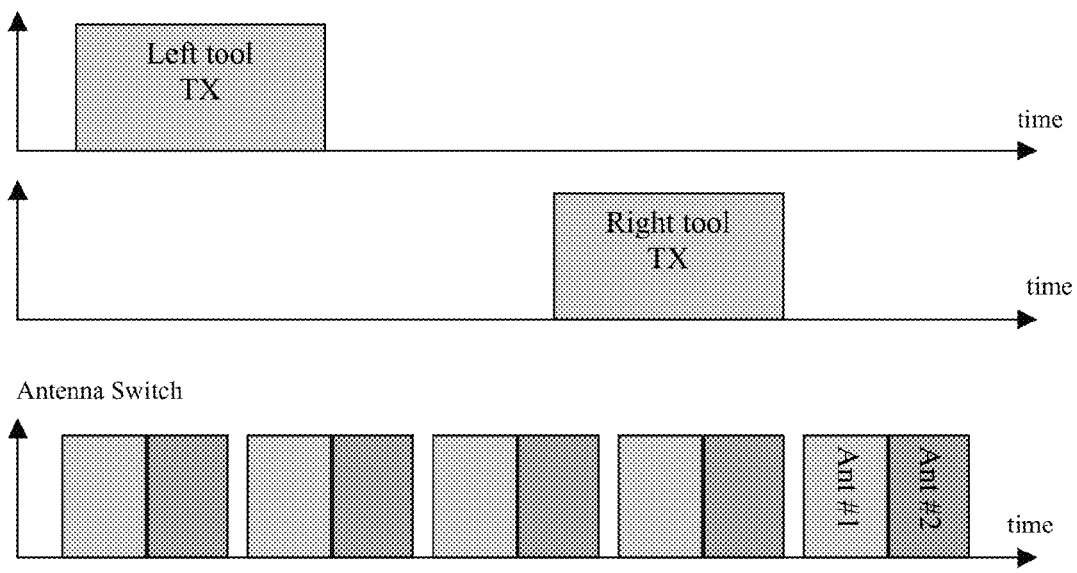
FIG. 6B shows the antenna switching pattern during sequential transmit operation.

In case of sequential transmission, each transmitter should be on for at least (N+1) X dwell intervals (receiver antenna dwell time). The antenna switch versus transmit sequential operation is shown in FIG. 6b.

In embodiments in which the two transmitters operate at different frequencies, the receiver scans all antenna patterns at the first frequency, then switches to the second frequency and scans all antenna patterns again, then returns to the first frequency, and so on.

Reference is now made to FIG. 7a, which illustrates an embodiment of the invention in which the directional antenna array has a planar structure. The short dipoles at each segment 72a,b,c are covered to protect the wires and the circuits from humidity and mechanical fractures. The arms 73a,b,c are made of any appropriate flexible material.

Reference is now made to FIG. 7b, which illustrates an embodiment of the invention in which the directional antenna array has a non-planar spatial structure. The fourth short dipole at segment 72d is not located in the plane that contains segments 72a,b,c. This arrangement allows the system to compute the spatial direction of the RF transmitter.

Figure 7C:
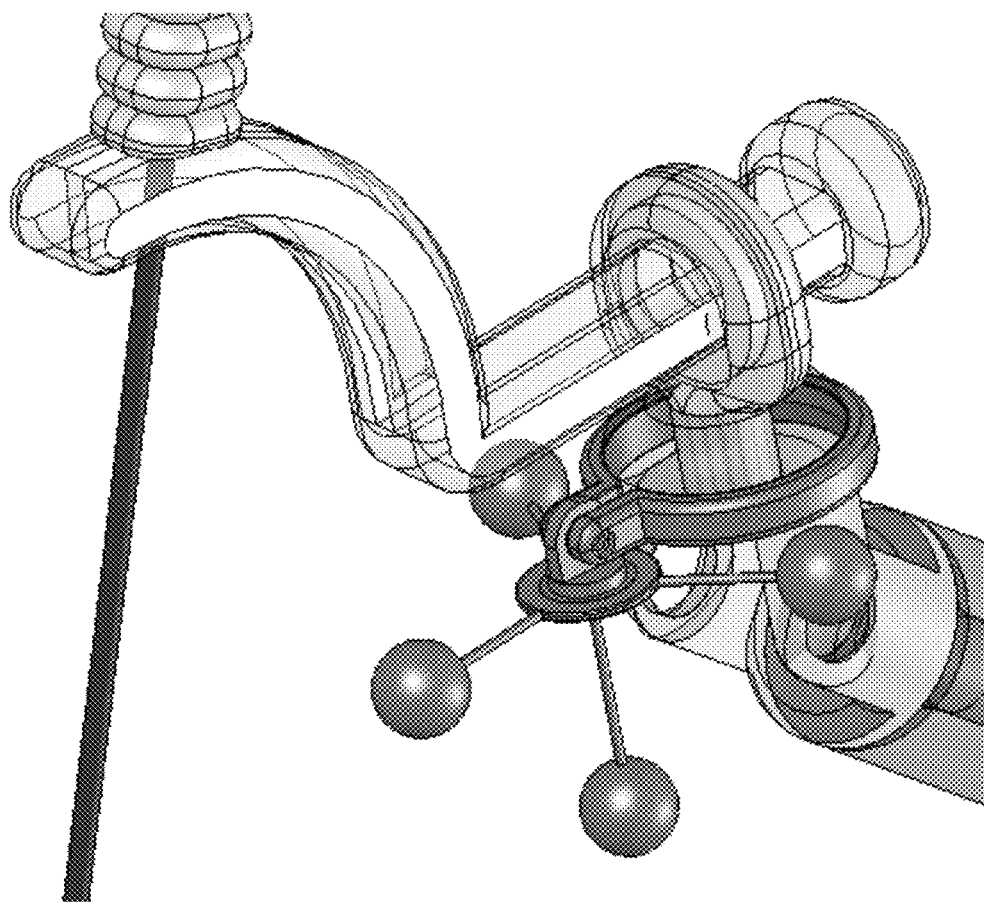
FIG. 7C shows an example of a spatial antenna mounted on the camera holder mechanism.

Reference is now made to FIG. 7c, which shows the antenna located on an automated automated assistant maneuvering system according to one embodiment of the invention.

Figure 8A:
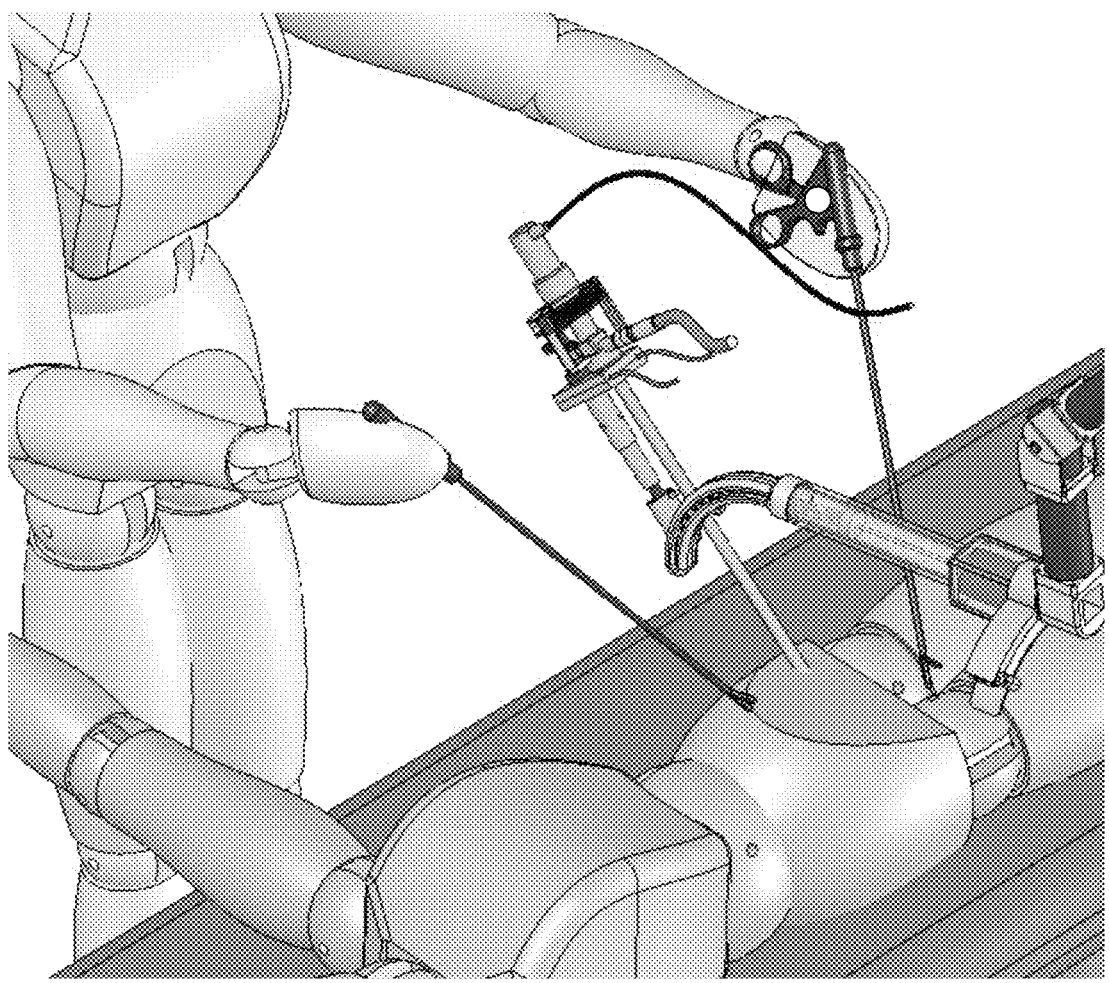
FIG. 8A shows an example of using the location system in abdominal laparoscopic surgery.

Reference is now made to FIGS. 8a,b,c, which illustrate in a non-limiting manner some types of surgeries in which the location system disclosed in the present invention can be utilized.

FIG. 8a shows an example of using the location system in abdominal laparoscopic surgery.

Figure 8B:
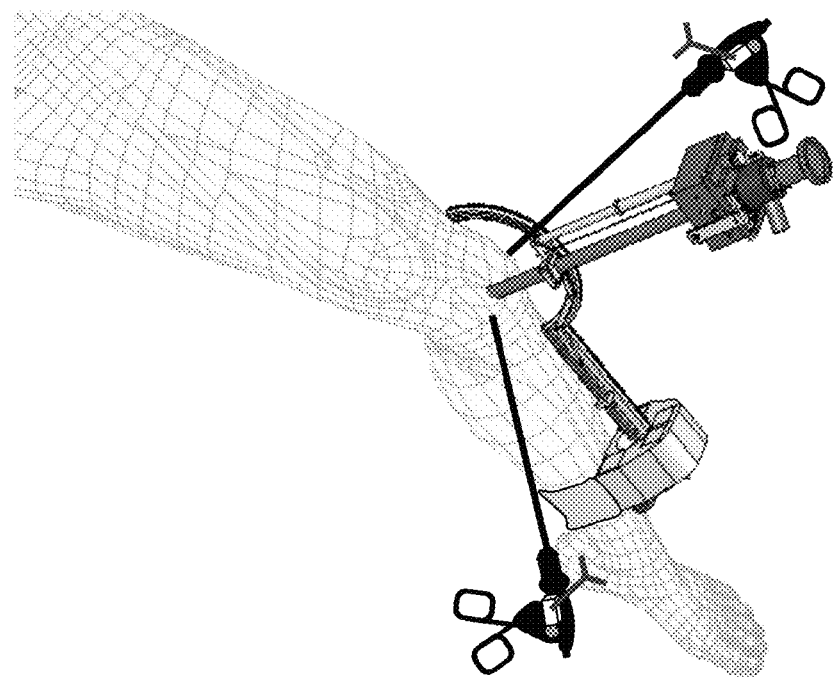
FIG. 8B shows an example of using the location system in knee endoscopic surgery; and, FIG. 8C shows an example of using the location system in shoulder endoscopic surgery.

FIG. 8b shows an example of using the location system in knee endoscopic surgery.

Figure 8C:
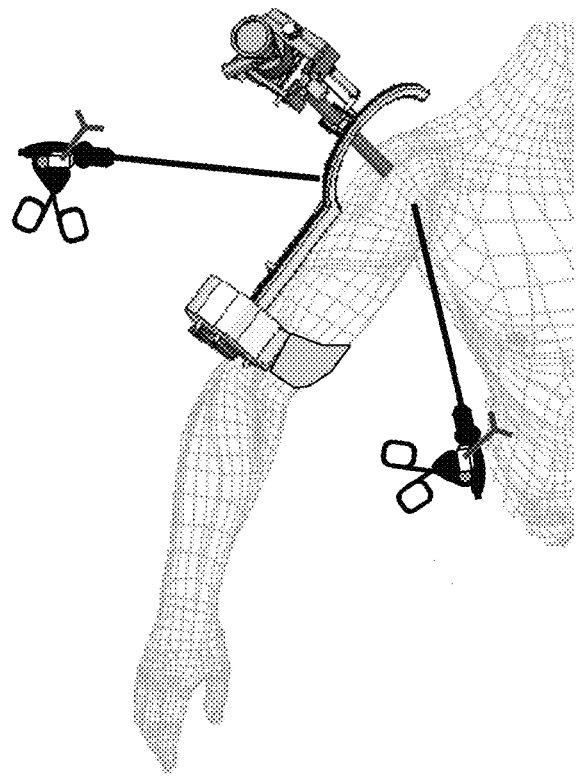

Lastly, FIG. 8c shows an example of using the location system in shoulder endoscopic surgery.

What is claimed is:

1. An interface between a surgeon and an automated assistant, comprising:
   a. at least one array comprising N RF transmitters, where N is a positive integer;
   b. one RF receiver provided with at least two co-located directional antenna; each of which is adapted to transmit a signal; each of said co-located directional antenna is characterized by an antenna Gain, Gr; each two co-located directional antenna are characterized by a predetermined dependency of the gain's ratio as a function of the direction from which said signal has been sent;
   c. means for attaching said RF transmitter array to at least one surgical tool; and,
   d. a computerized operating system adapted to record the received signal strength (RSS) received by each of said directional antenna of said one RF receiver; said interface is characterized by calculating the angle from which a signal had been received, by comparing said RSS received from all of said directional antenna in said RF receiver and the antenna's gain of each of said directional antenna according to the following equation RSS (directional antenna$_j$)/RSS(directional antenna$_k$) =Gr (antenna$_j$)/Gr(antenna$_k$), without the use of triangulation calculation; and further wherein the ration Gr(antenna$_j$)/Gr(antenna$_k$) is further characterized by known dependency of the angle from which said signal has been transmitted; said computerized operating system performing said calculations is adapted to provide automatically the results of said calculations to the automated assistant which controls said surgical tool of said interface.

2. The interface of claim 1, further comprising an endoscopic device; wherein said endoscopic device comprises optical imaging means, and further wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) the predicted appearance of said at least one surgical tool within said optical image; (g) if more than one of said at least one surgical tools appears simultaneously in said optical image, distinguishing among said more than at least surgical tools appearing in said optical image.

3. The interface of claim 1, further comprising
 a. an endoscopic device;
 b. an automate assistant for said endoscopic device; and
 c. means for interfacing said computerized operating system to said automated assistant;
 wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) a desired new location for said endoscopic device; (g) command protocol means for directing said automated assistant via said interface to maneuver said endoscopic device to a desired new location.

4. The interface of claim 3, wherein said endoscopic device comprises optical imaging means, and further wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) the predicted appearance of said at least one surgical tool within said optical image; (g) if more than one of said at least one surgical tools appears simultaneously in said optical image, distinguishing among said more than at least surgical tools appearing in said optical image; (h) a desired new location for said optical imaging means; (i) a command protocol for directing said automated assistant via said interface to maneuver said endoscopic device to a desired new location.

5. The interface of claim 4, wherein said computer controller additionally transmits a command protocol to said automated assistant via said interface to maneuver said endoscopic device to a desired new location.

6. The interface of claim 1, wherein said interface is adapted for automatic operation, whereby each of said N transmitters transmits continuously.

7. The interface of claim 1, wherein said interface is adapted for automatic operation, whereby each of said N transmitters transmits continuously, and further wherein said computer transmits said calculated parameters for each of said N transmitters in response to a command signal from the human operator of the interface.

8. The interface of claim 1, wherein said antenna array comprises at least one directional antenna.

9. The interface of claim 1, wherein said receiver array is adapted to determine the angle whose vertex is the location of said antenna array and which is subtended by the line connecting any two of said N transmitters.

10. The interface of claim 1, wherein said N RF transmitters transmit in the 430 MHz ISM band.

11. The interface of claim 1, wherein said transmitters transmit a modulated signal, said modulation chosen from the group consisting of (a) frequency modulation occurs around a frequency of about 1.5 kHz, (b) amplitude modulation.

12. The interface of claim 11, wherein each of said N RF transmitters is modulated at a different frequency.

13. The interface of claim 12, wherein said N modulated frequencies are spanning range of frequencies from about 1.0 kHz to about 1.5 kHz.

14. The interface of any one of claims 1, wherein said receiver is a single conversion receiver.

15. A method for providing the 3D positional parameters of a surgical tool, comprising the steps of
 a. obtaining an interface, comprising (i) at least one array comprising N RF transmitters, where N is a positive integer, (ii) one RF receiver provided with at least two co-located directional antenna; each of which is adapted to transmit a signal; each of said co-located directional antenna is characterized by an antenna Gain, Gr; each two co-located directional antenna are characterized by a predetermined dependency of the gain's ratio as a function of the direction from which said signal has been sent; (iii) a computerized operating system adapted to record the received signal strength (RSS) received by each of said directional antenna of said RF receiver;
 b. obtaining a surgical tool;
 c. attaching said RF transmitter array to said surgical tool;
 d. measuring the received signal strength (RSS) from said N RF transmitters received at each of said directional antenna of said RF receivers;
 e. calculating the angle from which the signal had been received according to a predetermined protocol;
 wherein said step of calculating the angle from which the signal had been received is characterized by comparing said RSS received from all of said directional antenna in said RF receiver and the antenna's gain of each of said directional antenna according to the following equation RSS(directional antenna$_j$)/RSS(directional antenna$_k$) = Gr(antenna$_j$)/Gr(antenna$_k$), without the use of triangulation calculation.

16. A method for controlling the position of an endoscopic device, comprising the steps of:
 a. obtaining an interface between a surgeon and an automated assistant, said interface comprising (i) at least one array comprising N RF transmitters, where N is a positive integer, (ii) one RF receiver provided with at least two co-located directional antenna; each of which is adapted to transmit a signal; each of said co-located directional antenna is characterized by an antenna Gain, Gr; each two co-located directional antenna are characterized by a predetermined dependency of the gain's ratio as a function of the direction from which said signal has been sent; (iii) a computerized operating system adapted to record the received signal strength (RSS) received by each of said directonal antenna of said RF receiver; (iv) an automated assistant for said endoscopic device; and, (v) means for interfacing said computerized operating system to said automated assistant;
 b. obtaining a surgical tool;
 c. attaching said RF transmitter array to said surgical tool;
 d. measuring the received signal strength (RSS) from said N RF transmitters received at each of said directional antenna of said RF receivers;
 e. calculating the angle from which the signal had been received according to a predetermined protocol;
 f. calculating a desired new position for said endoscopic device;
 g. sending a command from said computerized operating system to said automated assistant via said interfacing means to maneuver said endoscopic device to said desired new location; and, h. maneuvering said endoscopic device to said desired new location; thereby controlling said position of said endoscopic device;

wherein said step of calculating said parameters of each of said N transmitters yields positional parameters of said laparoscope surgical tool, said positional parameters is selected from a group consisting of (a) the angle from which the signal had been received; (b) the spatial location of said at least one surgical tool; (c) the path of said at least one surgical tool; (d) the spatial location of the tip of said at least one surgical tool; (e) matching each RF transmitter code with each calculated spatial location of said at least one surgical tool and/or said tip of said at least one surgical tool; further wherein said step of calculating said spatial parameters is characterized by comparing said RSS received from all of said directional antenna in said RF receiver and the antenna's gain of each of said directional antenna according to the following equation RSS(directional antenna$_j$)/RSS(directional antenna$_k$) =Gr(antenna$_j$)/Gr(antenna$_k$), without the use of triangulation calculation.

17. The method of claim 16, wherein said endoscopic device comprises optical imaging means, and further comprising the additional steps of
   a. determining said position of said surgical tool relative to the image frame according to a predetermined protocol;
   b. maneuvering said optical imaging means such that said surgical tool appears at a predetermined location within said image frame.

18. The method of claims 15, additionally comprising step of transmitting either a continuously or a non-continuously signal from each of said N transmitters in response to a signal from the human operator of said interface.

19. The method of claims 15, additionally comprising step of transmitting either a continuously or a non-continuously signal from each of said N transmitters in response to a signal from the human operator of said interface.

20. The interface of claim 1, wherein said computerized operating system is adapted to calculate at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; said computerized operating system performs said calculations and provides automatically the results of said calculations to the human operator of said interface.

* * * * *